Figure 1:
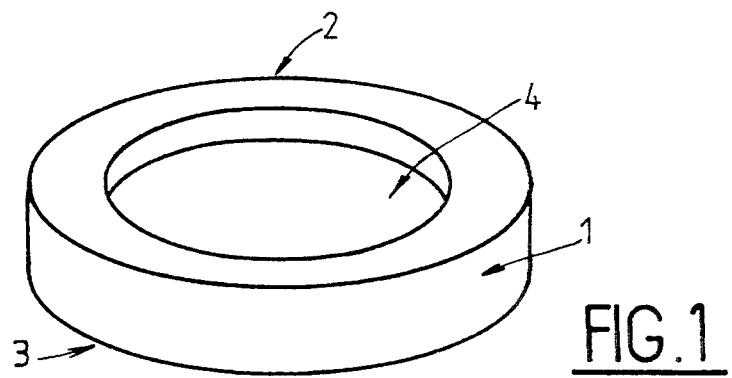

United States Patent [19]

Daoudal

[11] Patent Number: 5,411,735
[45] Date of Patent: May 2, 1995

[54] PASTILLE FOR FACILITATING THE INGESTION OF MEDICINAL TABLETS BY PETS

[75] Inventor: José Daoudal, Laval, France

[73] Assignee: Sogeval s.A., Laval Cedex, France

[21] Appl. No.: 73,595

[22] Filed: Jun. 8, 1993

[30] Foreign Application Priority Data

Jun. 9, 1992 [FR] France .................. 92 06908

[51] Int. Cl.$^6$ ............... A01N 25/24; A01N 25/34
[52] U.S. Cl. ................... 424/408; 424/405; 424/406; 424/407; 424/409; 514/918; 514/920; 514/974
[58] Field of Search ............. 424/408, 465 C, 469 C, 424/470 C, 473 C, 484 C, 405–407, 409; 514/920, 918, 974

[56] References Cited

FOREIGN PATENT DOCUMENTS 0320320  6/1989  European Pat. Off. .
2073278  1/1971  France .

OTHER PUBLICATIONS

Abstract-EP 0320320 (1989).

*Primary Examiner*—Jyothsna Venkat
*Attorney, Agent, or Firm*—Baker & Daniels

[57] ABSTRACT

Pastille for facilitating the ingestion of tablets, in particular medicinal tablets, by pets, in particular dogs or cats, characterized in that it consists of a matrix (1) which is made of a material which the animal finds appetizing and comprises two principal faces (2, 3) of which one (2) is provided with a recess (4) which, prior to being ingested, can receive a tablet (5) with a repellent smell and taste whilst the other, substantially smooth, face (3) is to be presented to the animal.

3 Claims, 1 Drawing Sheet

PASTILLE FOR FACILITATING THE INGESTION OF MEDICINAL TABLETS BY PETS

The present invention relates to a pastille for facilitating the ingestion of tablets, in particular medicinal tablets, by pets, in particular dogs or cats.

In the following, the term "pastille" is to be understood in a broad sense and is not restricted to the field of medicaments alone.

The number of pets such as dogs and cats is constantly increasing. At the same time, the care given to these animals is developing.

It should be noted that hitherto treatments administered have not always been continued faithfully owing to the difficulty involved in getting animals to ingest medication.

In fact it is well known that, owing to their smell, numerous medicinal substances are repellent to dogs or cats who refuse to ingest them, thus making it very difficult, or even impossible, to follow treatment.

In order to overcome this problem, in accordance with document EP-0 320 320 there has already been proposed a tablet which consists of at least one core containing one or more active principals which, owing to their smell, have a repellent effect on the animal, and which are totally encased in an appetising matrix.

This tablet has proved satisfactory in that it can be ingested spontaneously by the animal but at the same time it has the disadvantage that it is particularly awkward in view of the need to provide an encasing process specific to each type of tablet, resulting in a notable increase in the cost of veterinary treatments.

In addition, in order that all dog and cat owners can benefit from the advantages of this tablet, its manufacture would have to be generalised such that all laboratories manufacturing tablets, in particular of a medicinal nature for dogs or cats, were able to perform an encasing process, which is difficult to envisage; in addition there is currently on the market a stock of tablets which cannot be encased.

The object of the present invention is to overcome these disadvantages by proposing a pastille enabling the ingestion of tablets, in particular medicinal tablets, by pets, in particular dogs or cats, to be facilitated, by virtue of which the encasing operation can, to a certain extent, be performed by the pet owner himself when the active principal is administered.

This pastille is characterised in that it consists of a matrix made of a material which the animal finds appetising and comprises two principal faces of which one is provided with a recess which, prior to ingestion, can receive a tablet with a repellent smell and taste, whilst the other, substantially smooth, face is to be presented to the animal.

It has unexpectedly been noted that the pastille according to the invention is ingested spontaneously by dogs and cats despite the fact that the active tablet is still visible on the rear face of the pastille.

It will be appreciated that it is possible to hold the tablet in the recess in any manner and in particular using an adhesive substance.

A further possibility consists in giving the recess a shape and dimensions corresponding to those of the tablet such that the latter can be inserted and held by force in the appetising matrix.

In accordance with a preferred characteristic of the invention, however, the recess is frustoconical such that all types of tablet can be inserted by force and held in the appetising matrix.

It is evident that the pastille according to the invention is such that it considerably reduces the cost of medicinal treatments for dogs and cats. Each pet owner can purchase a batch of pastilles which he can then "equip" with tablets as required.

In a manner known per se, in studies of the factors governing appetence for dogs and cats, it has been found that powdered liver is particularly prized by these animals and that a mixture of powdered liver and brewer's yeast can to a large extent facilitate the ingestion of medicaments by dogs and cats, thus enabling preventive or curative treatments to be administered easily to them.

For this reason, the appetising matrix according to the invention can advantageously contain a mixture of powdered liver and brewer's yeast. More precisely, the materials cited in above-mentioned document EP-0 320 320 can be used to produce this matrix.

It will be appreciated that the shape of the matrix according to the invention does not restrict the invention. However, in general, the shape of a disc and in particular of a disc of which the two principal faces are slightly convex is chosen, this shape, which is the same as the vast majority of medicinal tablets in particular, proving to be particularly advantageous for reasons of facility of manufacture.

Figure 2:
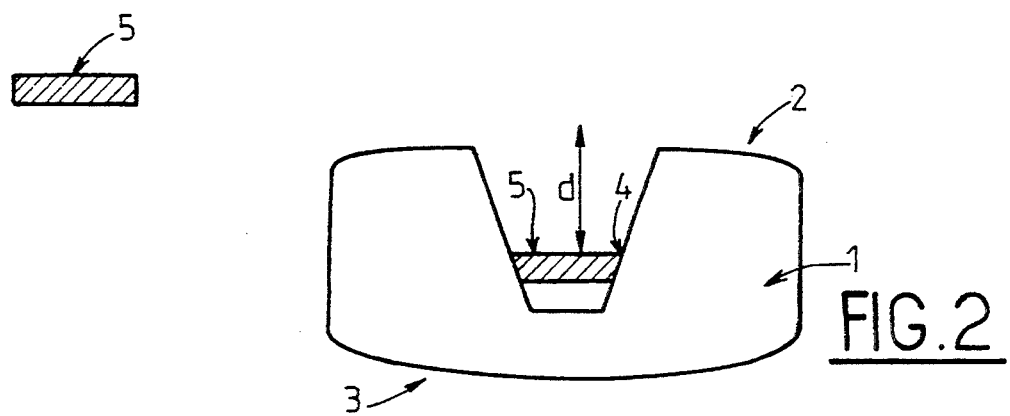
Figure 3:
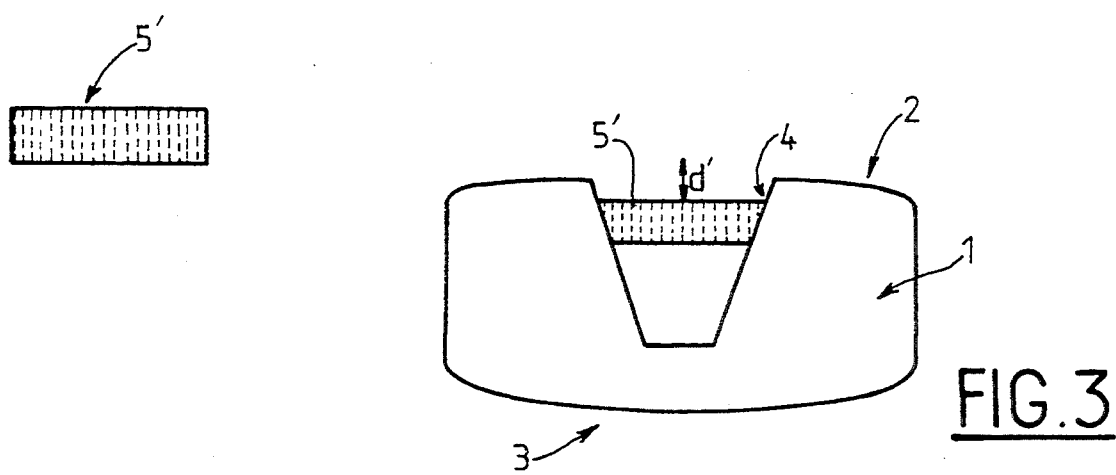

The characteristics of the pastille to which the invention relates are described in greater detail with reference to the attached drawings, in which:

FIG. 1 is a view in perspective of the pastille before the tablet is put in place; and FIGS. 2 and 3 are views in section through a diametric plan of a pastille "equipped" with a tablet.

It should be noted that the scale of the Figures has been greatly enlarged and that the pastilles preferably have a diameter of approximately 20 mm in order to correspond to the dimensions of tablets conventionally available.

In accordance with FIGS. 1 to 3, the pastille 1 according to the invention consists of a disc-shaped matrix consisting of a material containing a mixture of powdered liver and brewer's yeast which has proved to be particularly appetising for pets such as dogs and cats.

This matrix 1 comprises two principal faces 2 and 3 which are slightly convex.

In accordance with the non-limiting example shown in FIGS. 2 and 3, the principal face 2 is provided with a frustoconical recess 4 for receiving a tablet 5, 5' (FIGS. 2 and 3) in particular a medicinal tablet inserted by force by the pet owner when the medicament is to be administered.

When used, the pastille is presented to the animal with its face 3 turned towards the latter and can thus be easily ingested.

By virtue of a frustoconical shape being chosen, the recess 4 can be adapted to tablets of different dimensions: the tablet 5' inserted in the recess 4, in accordance with FIG. 3, is far larger than the tablet shown in FIG. 2 and can nevertheless be held perfectly.

It will be appreciated that the depth of penetration d, d' of the tablet 5, 5' in the recess 4 depends on its dimensions and is lower in the case of a large tablet.

I claim:

1. Pastille for facilitating the ingestion of a tablet by a pet, the tablet having a repellant smell and taste, said pastille comprising:

a matrix made of a material which is appetizing to the pet, having two principal faces, one of said faces having a recess for receiving the tablet, and the other of said faces being substantially smooth and adapted for presentment to the pet, said recess having a frustoconical shape and dimensions corresponding to those of the tablet, whereby tablets of different dimensions can be inserted by force and held in the appetizing matrix wherein said Pastille is substantially disc shaped.

2. Pastille according to claim 1, wherein the appetizing matrix contains a mixture of powdered liver and brewer's yeast.

3. Pastille according to claim 1, wherein the two principal faces are slightly convex.

* * * * *